(12) United States Patent
Brandeis

(10) Patent No.: US 8,758,384 B2
(45) Date of Patent: Jun. 24, 2014

(54) INTRAVASCULAR DEVICES FOR TREATING BLOOD VESSELS AND A METHOD OF USING SUCH DEVICES

(75) Inventor: Zeev Brandeis, Rosh HaAyin (IL)

(73) Assignee: V. V. T. Med Ltd., Kfar-Saba (IL)

( * ) Notice: Subject to any disclaimer, the term of this patent is extended or adjusted under 35 U.S.C. 154(b) by 200 days.

(21) Appl. No.: 13/021,813

(22) Filed: Feb. 7, 2011

(65) Prior Publication Data

US 2011/0196468 A1    Aug. 11, 2011

Related U.S. Application Data

(60) Provisional application No. 61/302,143, filed on Feb. 7, 2010, provisional application No. 61/302,141, filed on Feb. 7, 2010.

(51) Int. Cl.
 *A61M 29/00* (2006.01)
(52) U.S. Cl.
 USPC .......................................... 606/191; 606/200
(58) Field of Classification Search
 USPC ......... 606/191, 192, 193, 194, 195, 196, 197, 606/198, 199, 200, 213, 158
 See application file for complete search history.

(56) References Cited

U.S. PATENT DOCUMENTS

| | | | |
|---|---|---|---|
| 5,370,657 A | | 12/1994 | Irie |
| 5,683,411 A | | 11/1997 | Kavteladze et al. |
| 5,836,968 A | * | 11/1998 | Simon et al. ................ 606/200 |
| 6,267,783 B1 | | 7/2001 | Letendre et al. |
| 6,551,340 B1 | | 4/2003 | Konya et al. |
| 6,752,819 B1 | * | 6/2004 | Brady et al. ................ 606/200 |
| 8,088,140 B2 | | 1/2012 | Ferrera et al. |
| 2004/0098030 A1 | * | 5/2004 | Makower et al. ............ 606/200 |
| 2004/0153120 A1 | | 8/2004 | Seifert et al. |
| 2005/0038470 A1 | | 2/2005 | Van der Burg et al. |
| 2005/0222604 A1 | | 10/2005 | Schaeffer |
| 2008/0119867 A1 | | 5/2008 | Delaney |
| 2008/0294188 A1 | | 11/2008 | Appling et al. |
| 2009/0131870 A1 | | 5/2009 | Fiser |
| 2009/0131970 A1 | | 5/2009 | Chanduszko et al. |
| 2010/0010532 A1 | | 1/2010 | Vallabhaneni |
| 2010/0324585 A1 | * | 12/2010 | Miles et al. ................... 606/198 |

FOREIGN PATENT DOCUMENTS

WO    WO 2006/017470    2/2006

OTHER PUBLICATIONS

Communication Pursuant to Rules 70(2) and 70a(2) EPC and Reference to Rule 39(1) EPC Dated Aug. 16, 2011 From the European Patent Office Re. Application No. 11153553.0.
Communication Pursuant to Rules 70(2) and 70a(2) EPC and Reference to Rule 39(1) EPC Dated Aug. 16, 2011 From the European Patent Office Re. Application No. 11153565.4.
European Search Report and the European Search Opinion Dated May 25, 2011 From the European Patent Office Re. Application No. 1115365.4.
European Search Report and the European Search Opinion Dated May 26, 2011 From the European Patent Office Re. Application No. 1115365.4.
Official Action Dated Jul. 17, 2013 From the US Patent and Trademark Office Re. U.S. Appl. No. 13/021,817.

\* cited by examiner

*Primary Examiner* — Katherine Dowe
*Assistant Examiner* — Katrina Stransky

(57) ABSTRACT

A medical implant for occluding a blood vessel. The medical implant comprises a cup shaped elastic blood impermeable membrane sized and shaped for substantially occluding a lumen of a blood vessel, at least one scaffolding element mounted, sized and shaped for being attached at least one blood clot forming in front of the elastic blood impermeable membrane, and at least one anchoring element having a tip directed outward from the center of the cup shaped elastic blood impermeable membrane.

17 Claims, 3 Drawing Sheets

INTRAVASCULAR DEVICES FOR TREATING BLOOD VESSELS AND A METHOD OF USING SUCH DEVICES

RELATED APPLICATIONS

This application claims the benefit of priority under 35 USC 119(e) of U.S. Provisional Patent Application Nos. 61/302,143 and 61/302,141, both filed on Feb. 7, 2010. The contents of the above applications are incorporated herein by reference in their entirety.

FIELD AND BACKGROUND OF THE INVENTION

The present invention, in some embodiments thereof, relates to a vein treatment and, more particularly, but not exclusively, to intravascular devices for treating veins and a method of using such devices.

Sclerotherapy, along with surgery, radiofrequency and laser ablation, are procedures used to treat blood vessels or blood vessel malformations (vascular malformations) and also those of the lymphatic system. In Sclerotherapy, a sclerosing solution is injected into the vessels, causes the target blood vessel to immediately shrink, and then dissolve over a period of weeks as the body naturally absorbs the treated vein. It is used for children and young adults with vascular or lymphatic malformations.

During the last years, some vessel blocking devices and methods have been developed, inter alia, to support the sclerotherapy. For example, U.S. Pat. No. 5,683,411 filed on Oct. 19, 1995 describes a medical article for implantation into the vascular system of a patient comprises a self expanding body shaped substantially into the form of a body of revolution, at least part of the surface of which is defined by wire members forming cells of a generally polygonal shape. The body of revolution has a diameter increasing continuously in an axial direction of the body from one end forming an apex towards the opposite end forming a base (S). The article may comprise two bodies of revolution joined at their apices. The article may be used, in particular as an intravenous filter for the capture of thrombi or in combination with an elastic blood impermeable membrane flexibly linked to the apex of the body of revolution as an occlusion device for closing a vessel lumen or defects such as ASD or PDA in vascular walls.

Another example is provided in International Patent Application No. WO 20061017470 describes a device and method for treating bodily diseases and/or conditions, for example, varicose veins, tumors and aneurisms including for example insertion of a blocking device toward a target destination using a catheter and delivery of sclerosing or other agents to the vessel while maintaining minimal, for example zero pressure in the treatment area. The blocking device may prevent treatment materials, embolisms, debris and the like, from entering the upstream section of vessel. The blocking device may include, for example, a cap or other concave shape and may be expandable or extendible towards the vessel walls.

SUMMARY OF THE INVENTION

According to some embodiments of the present invention there is provided a medical implant for occluding a blood vessel. The medical implant comprises a cup shaped elastic blood impermeable membrane sized and shaped for substantially occluding a lumen of a blood vessel, at least one scaffolding element mounted, sized and shaped for being attached at least one blood clot forming in front of the elastic blood impermeable membrane, and at least one anchoring element having a tip directed outward from the center of the cup shaped elastic blood impermeable membrane.

Optionally, the elastic blood impermeable membrane is conical.

Optionally, the at least one scaffolding element is mounted in a space encircled by the cup shaped elastic blood impermeable membrane.

Optionally, the at least one anchoring element comprises a plurality of hooks set to stick in the inner wall of the lumen.

More optionally, the medical implant further comprises a support element configured to hold the elastic blood impermeable membrane in a conical structure and the at least one scaffolding element in a space encircled by the conical structure.

Optionally, the elastic blood impermeable membrane comprises a porous film.

Optionally, the elastic blood impermeable membrane comprises a non-woven fabric selected from a group consisting of Polyurethane, Polyethylene, Polyamide and expanded Polytetrafluoroethylene (PTFE).

Optionally, the medical implant further comprises an engagement element for mechanically and detachably connecting the medical implant to a pivot of a delivery device.

Optionally, the elastic blood impermeable membrane having a first cup shape in a compressed state and a second cup shape in an uncompressed state, the first cup having a smaller diameter than the second cup shape.

Optionally, the at least one anchoring element have a tilted state wherein a distal end thereof is tilted away from a longitudinal axis crossing the center of the cup shaped elastic blood impermeable membrane and a vertical state wherein the at least one anchoring element is proximate to the longitudinal axis.

According to some embodiments of the present invention there is provided a medical implant for occluding a blood vessel. The medical implant comprises a conical elastic blood impermeable membrane, at least one scaffolding element mounted within a space encircled by the conical elastic blood impermeable membrane, a supporting element for holding the at least one scaffolding element at the center of the conical elastic blood impermeable membrane, and a plurality of tilted hooks each having a proximal end attached to the supporting element and a distal end tilted outward from a longitudinal axis crossing via the center of the conical elastic blood impermeable membrane.

According to some embodiments of the present invention there is provided a method for occluding a blood vessel. The method comprises conducting a medical implant having an elastic blood impermeable membrane in a compressed state and at least one scaffolding element to an intravascular target area in a blood vessel, placing the medical implant in the intravascular target area, and occluding the vessel by spreading the elastic blood impermeable membrane from the compressed state to an uncompressed state in the intravascular target area. The at least one scaffolding element is sized and shaped to be attached to at least one blood clot formed at the intravascular target area so that the at least one blood clot being firmly attached to the medical implant.

Optionally, the at least one scaffolding element induces encapsulation of the medical implant in the intravascular target area.

Optionally, the conducting comprises loading the medical implant into a catheter and using the catheter for performing the conducting.

Optionally, the loading comprises: placing the medical implant in an adaptor, connecting an adaptor to a distal end of a catheter, and pulling the medical implant into the catheter, and removing the adaptor from the distal end.

More optionally, the pulling comprises pulling the medical implant into a magazine in the catheter.

Optionally, medical implant is stored prior to delivery in a non compressed state.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
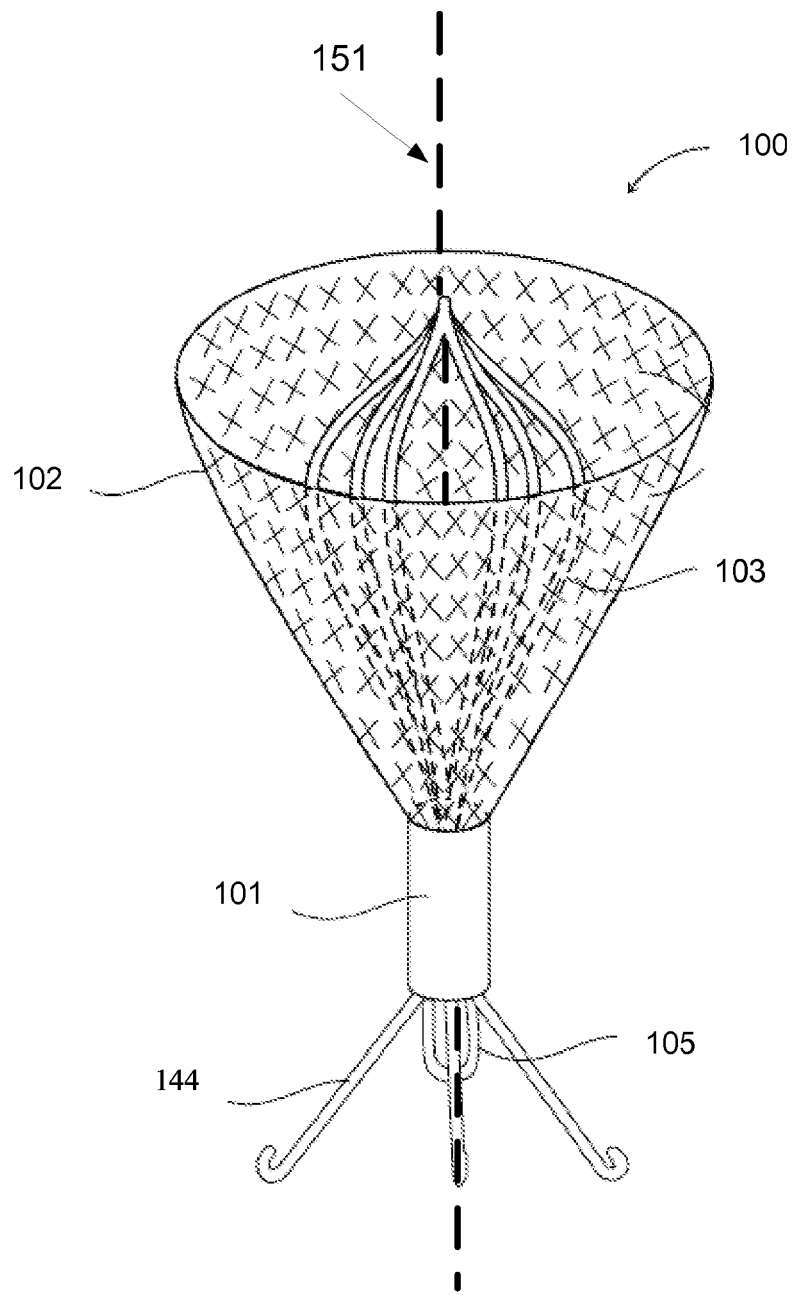
FIG. 1 is a schematic illustration of a medical implant of occluding a blood vessel, according to some embodiments of the present invention.

The present invention, in some embodiments thereof, relates to a vein treatment and, more particularly, but not exclusively, to intravascular devices for treating veins and a method of using such devices.

According to some embodiment of the present invention, there is provided a medical implant of occluding a blood vessel. The medical implant includes a cup shaped elastic blood impermeable membrane that is sized and shaped for substantially occluding a lumen of a blood vessel, such as a vein, for example during varicose vein treatments, such as sclerotherapy. The elastic blood impermeable membrane is set to be compressed so as to allow the conducting thereof in a tubular conducting element, such as a catheter. The medical implant further includes one or more scaffolding elements shaping the coagulation in proximity to the cup shaped elastic blood impermeable membrane. The scaffolding elements are set to be attached to blood clot(s) formed in front of the elastic blood impermeable membrane. The scaffolding elements are optionally elastic to allow the conducting thereof in a tubular conducting element, such as a catheter. The medical implant further includes anchoring element(s) having their tip directed outward from the center of the cup shaped elastic blood impermeable membrane, for example away from longitudinal axis crossing through the center of the cup shaped elastic blood impermeable membrane.

According to some embodiment of the present invention, there is provided a method of occluding a blood vessel using a medical implant, for example as outlined above and described below. The method is based on using a catheter device for conducting the medical implant to an intravascular target area in a blood vessel. Optionally, before the conducting, the medical implant is loaded into the distal end of the catheter device. The loading is optionally performed using an adapter that is connected to the distal end of the catheter device and allows pulling the medical implant thereinto. After the medical implant is conducted to a target intravascular area, it is released from the catheter device. The release induces the spreading of the elastic blood impermeable membrane and optionally of the anchoring elements and/or the one or more scaffolding elements. In such a manner, the blood vessel is occluded at the target intravascular area and the scaffolding element(s) shape the coagulation in proximity thereto so that formed blood clot(s) are firmly attached to the medical implant.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Reference is now made to FIG. 1, which is a schematic illustration of a medical implant 100 of occluding a blood vessel, according to some embodiments of the present invention.

The medical implant 100 includes a support element 101, such as a clamp and a ring shaped element, which is set to attach and support the components of the medical implant 100 together. The support element 101 may comprise one or more components. The support element 101 is mechanically connected to an elastic blood impermeable membrane 102, optionally cup shaped, for example conical, which is sized and shaped for substantially occluding a lumen of a blood vessel when stretched to form an open structure. As used herein impermeable means 100% impermeable to blood and substantially impermeable, for example 90% impermeable to blood or more. The blood impermeable membrane 102 is optionally made of a non-woven fabric such as Polyurethane, Polyethylene, Polyamide and expanded Polytetrafluoroethylene (PTFE). The blood impermeable membrane 102 is substantially impervious to fluid. Optionally, as depicted in FIG. 1, the clamp 101 holds the tip of an elastic blood impermeable membrane 102 so as to maintain its form in a conical structure. Optionally, the blood impermeable membrane 102 has an uncompressed state wherein the diameter thereof is fit to occlude the lumen of a blood vessel and a compressed state wherein the diameter thereof is smaller and set to be placed in a tubular conducting device such as a catheter. Optionally, unlike a shape memory blocking elements, when the elastic blood impermeable membrane 102 is in an uncompressed state it does not apply extensive pressure on the surrounding tissues. The elastic blood impermeable membrane 102, which has a relatively flexible structure, tends to compress, rather than expend, during a period of more than few weeks. In such a manner, when the elastic blood impermeable membrane 102 is deployed to occlude the target blood vessel, the pressure it applies on the surrounding tissues is reduced over time.

The clamp 101 supports one or more scaffoldings elements 103, such as bended arms, optionally in front of the impermeable membrane 102, for example at center of the cup shaped structure it forms. Optionally, the gap between the arms is between 1 mm and 6 mm, in accordance with a required functionality and/or the target position at which the medical implement 100. Other sizes and dimensions may be used. Optionally, the scaffoldings elements 103 are constructed from shape memory materials, such as nickel titanium (Nitinol), to enable automatic spreading in an intravascular target area according to a controlled degree. As the scaffolding elements are bound in a space formed within the cup shaped elastic blood impermeable membrane, it does not apply pressure on the surrounding tissues. However as the scaffolding elements are made of shape memory material, their structure remains relatively stable even after the elastic blood impermeable membrane collapses. The scaffoldings elements 103 are sized and shaped for forming a blood clot in front of the elastic blood impermeable membrane 102 when the elastic blood impermeable membrane 102 substantially occludes the lumen of a hosting target vein. In particular, the occluding of a blood vessel obstructs normal blood flow therethrough, triggering coagulation in proximity to the medical implant 100 and the encapsulation of the medical implant 100 by body tissue, for example endothelium. The scaffoldings elements 103 encourage the binding of clots forming in proximity to the medical implant 100 to the medical implant 100. In such a manner, the migration of clots, which are formed in proximity to the medical implant 100, is prevented or reduced as the clots are bind with the medical implant 100. The scaffoldings elements 103 encourage the encapsulation of the medical implant 100.

The medical implant 100 further includes, for examples shown at 104, anchoring element(s). Optionally, each anchoring element 144 has a tilted state in which it is tilted outward, for example as depicted in FIG. 1, and a vertical state wherein it is placed in proximity to a longitudina axis 151 crossing the medical implant 100, for example passing along the center of the clamp 103 and/or the cup shape structure of the blood impermeable membrane 102. Optionally, a proximal end of each anchoring element 144 is supported by to the support element 101 and a distal end is bended to form and/or includes a hook directed outward from the longitudinal axis 151. In such a manner, when the medical implant 100 is placed in an intravascular target area and the anchoring elements 144 are in a tilted state, the distal ends of the anchoring elements 144 are directed toward the walls of the target blood vessel. Optionally, the anchoring elements 144 are constructed from shape memory materials, such as nickel titanium (Nitinol), to enable automatic spreading in an intravascular target area according to a controlled degree.

The medical implant 100 further includes, for example as shown at 105, a fastening element, such as a hitch, a loop, and/or a hook, for attaching the medical implant 100 to a maneuvering device, such as a pivot of a delivery rod which is threaded via a catheter. The fastening element allows retrieving into a conducting catheter and/or guiding the medical implant 100 via and/or in a conducting catheter. Optionally, the fastening element 105 is set to be connected to a pivot 355 as described in cofiled international patent application titled coupling devices for interventional delivery systems and methods of using such coupling devices, which is incorporated herein by reference and claims priority from U.S. provisional patent application No. 61/302,141, filed on Feb. 7, 2010, which is also incorporated herein by reference.

When the medical implant 100 is deployed at an intravascular target area, for example as part of a blood vessel treatment, such as varicose vein treatments and sclerotherapy, blood particles, emboli, debris and/or particles resulting from the blood vessel treatment are occluded by the medical implant 100. When the medical implant 100 is placed downstream from a treatment area, the occluding prevents from blood particles, emboli, debris and/or particles from getting into the blood stream during and/or after vein treatment procedures.

Optionally, the medical implant 100 is used to prevent re-canalization following vein treatment, for example by sealing the blood flow in the blood vessel.

Figure 2:
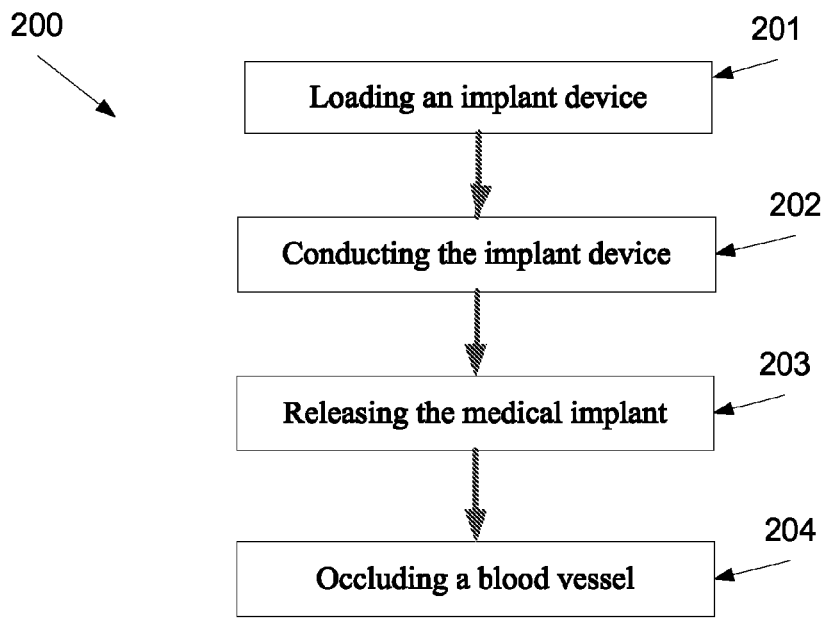
FIG. 2 is a flowchart of a method of using a medical implant, such as the medical implant depicted in FIG. 1, for occluding a blood vessel, according to some embodiments of the present invention.

Reference is now made to FIG. 2, which is a flowchart of a method 200 of using a medical implant, such as the medical implant 100 depicted in FIG. 1, for occluding a blood vessel, according to some embodiments of the present invention.

Figure 3:
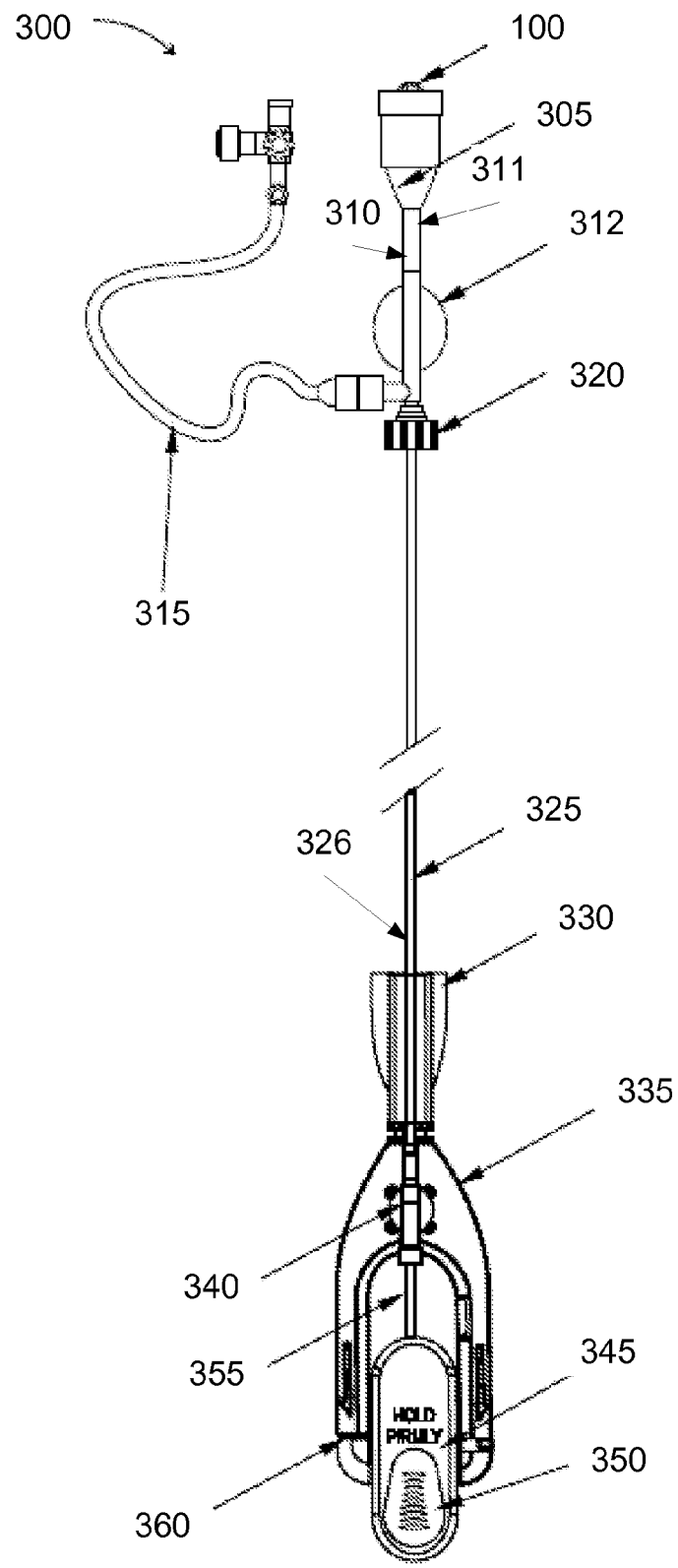
FIG. 3 is a schematic illustration of an interventional delivery system for implanting a medical implant, such as the medical implant of FIG. 1, in an intravascular target area of a target blood vessel, according to some embodiments of the present invention.

First, as shown at 201, the medical implant 100 is loaded into an interventional delivery system, for example a catheter based system. For example, reference is now also made to FIG. 3, which is a schematic illustration of an interventional delivery system 300 for implanting a medical implant, such as the medical implant 100, in an intravascular target area of a target blood vessel, according to some embodiments of the present invention. The interventional delivery system 300 has a delivery rod 325 having a pivot and a channel and set to be threaded via a catheter 310 (length is not to scale) toward the intravascular target area. The lumen of the catheter 310 and the distal end thereof 311 is sized and shaped to contain the medical implement 100 wherein the blood impermeable membrane 102 is in a compressed state and optionally the anchoring elements 144 are in a vertical state. Optionally, the catheter's distal end 311 is detachably connected to an adaptor 305 for supporting the loading of a medical implant, such as the medical implant 100. The adaptor 305 is set to contain the medical implant 100 with the blood impermeable membrane 102 in an uncompressed state and optionally the anchoring elements 144 are in a tilted state. When stored, the elastic blood impermeable membranes 102 are optionally stored in adaptors 305. In such an embodiment, the medical implant 100 is separated from the interventional delivery system 300. During the loading, the detachable adaptor 305 is attached to the catheter's distal end 311 to allow the pulling of the medical implant 100 into the catheter 310 via the catheter's distal end 311. Optionally, the medical implant 100 is pulled toward a magazine 312 for example in proximity to the proximal end of the catheter 310. The pulling is optionally done by connecting the medical implant 100 to the distal end of the pivot of the delivery rod 325, for example using the fastening element 105 and retrieving the delivery rod 325 while the catheter remains in place. After the loading, the detachable adaptor 305 is removed, for example before the implantation process. Optionally, the medical implant is retrieved into the channel of the delivery rod 325.

Now, as shown at 202, the medical implant 100 is conducted to a target area via the vascular system, using the catheter based system such as the interventional delivery system 300. Reference is now made to a description of optional elements of the interventional delivery system 300. Optionally, the interventional delivery system 300 includes a side port 315 for flushing, injecting or suctioning of liquids or other materials via the catheter 310. The side port may be used for connecting to one or more delivery syringes or additional catheters to the catheter 310. A screw valve 320 may be provided to connect between the delivery rod 325 and the catheter 310, creating a hermetic seal. The delivery rod 325 optionally includes a channel 326 and a pivot 355, such as a wire, which is typically covered or coated, for example, by a polymer. Such a coating provides a supportive structure to the pivot 355. One end of the pivot 355 is mechanically and detachably coupled to the medical implant 100, for example to the fastening element 105, via the catheter 310.

Optionally, a safety latch 330 is used to prevent the releasing of the pivot 355 from the channel 326 and/or to stop unintended or premature releasing or deploying of the pivot 355 from the delivery catheter 310. A delivery rod handle 335 is connected to control and maneuver the pivot 355 in or in relation to the channel 326. The delivery rod handle 335 includes a delivery rod Luer lock 340 (i.e. female), and a push wire grip 345, with a push wire gripping mechanism 350 are provided, to enable controlled locking and releasing actions. Optionally, a safety pin 360 is threaded via the push wire gripping mechanism 350 to prevent undesired release of the medical implant 100 from the delivery rod 325, prior to final positioning of the catheter's distal end 311 at the intravascular target area for deployment. Delivery rod handle 335 is optionally connected to distal part of the delivery rod 325.

As shown at 203, the medical implant 100 is released after being conducted to the intravascular target area in a blood vessel, for example using the interventional delivery system 300. When the interventional delivery system 300 is used, the deployment of the medical implant 100, when the catheter's distal end 311 arrived to the intravascular target area, is performed by removing and/or breaking the safety latch 330 to advance the tip of the delivery rod 325 beyond the catheter's distal end 311, thereby to place or position the medical implant 100 in the target vascular area, for example under ultrasonic and/or other suitable guidance. At this point, the medical implant 100 may be still connected to the interventional delivery system 300 and therefore may be repositioned and/or fully retrieved using the retrieval element. After the medical implant is positioned, a safety pin (not shown), if used, is removed from the delivery rod handle 335. This allows retrieving the channel 326 of the delivery rod 325 while maintaining the pivot 355 with the medical implant in place or pushing the pivot 355 with the medical implant while maintaining the channel 326 of the delivery rod 325 in place. This action releases the anchoring elements q144 in the target area, thereby allowing for full deployment of the medical implant 100 at a selected position. Now, the push wire Luer lock 340 may be released from the delivery rod handle and the delivery rod handle 335 may be discarded.

As shown at 204, by deploying the medical implant 100 in the intravascular target area and triggering the spreading of the elastic blood impermeable membrane 102, the target blood vessel is occluded. The releasing of the medical implant 100 from the catheter's distal end 311 allows the elastic blood impermeable membrane 102 to switch from a compressed state to an uncompressed state. Now, the scaffolding element(s) 103 may trigger coagulation at the intravascular target area so that the formed blood clot(s) are firmly attached to the implanted medical implant 200.

It is expected that during the life of a patent maturing from this application many relevant devices and methods will be developed and the scope of the term an anchoring element, a shape memory material, and a catheter, is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A medical implant for occluding a blood vessel, comprising:
   a cup shaped elastic blood impermeable membrane sized and shaped for substantially occluding a lumen of a blood vessel;
   at least one scaffolding element mounted, sized and shaped for being attached at least one blood clot forming in front of said elastic blood impermeable membrane; and
   at least one anchoring element having a tip directed outward from the center of the cup shaped elastic blood impermeable membrane;
   wherein said at least one scaffolding element is extended from said cup shaped elastic blood impermeable membrane along a longitudinal axis traversing a center of a cup shaped space encircled by said cup shaped elastic blood impermeable membrane said at least one scaffolding element comprising a plurality of bended arms connected together at a proximal end and a distal end of the at least one scaffolding element along the longitudinal axis.

2. The medical implant of claim 1, wherein said cup shaped elastic blood impermeable membrane is conical.

3. The medical implant of claim 1, wherein said at least one scaffolding element is mounted in a space encircled by said cup shaped elastic blood impermeable membrane.

4. The medical implant of claim 1, wherein said at least one anchoring element comprises a plurality of hooks set to stick in the inner wall of said lumen.

5. The medical implant of claim 2, further comprising a support element configured to hold said elastic blood impermeable membrane in a conical structure and said at least one scaffolding element in a space encircled by said conical structure.

6. The medical implant of claim 1, wherein said elastic blood impermeable membrane comprises a porous film.

7. The medical implant of claim 1, wherein said elastic blood impermeable membrane comprises a non-woven fabric selected from a group consisting of Polyurethane, Polyethylene, Polyamide and expanded Polytetrafluoroethylene (PTFE).

8. The medical implant of claim 1, further comprising an engagement element for mechanically and detachably connecting said medical implant to a pivot of a delivery device.

9. The medical implant of claim 1, wherein said elastic blood impermeable membrane having a first cup shape in a compressed state and a second cup shape in an uncompressed state, said first cup having a smaller diameter than said second cup shape.

10. The medical implant of claim 1, wherein said at least one anchoring element have a tilted state wherein a distal end thereof is tilted away from a longitudinal axis crossing the center of said cup shaped elastic blood impermeable membrane and a vertical state wherein said at least one anchoring element is proximate to said longitudinal axis.

11. A medical implant for occluding a blood vessel, comprising:
    a conical elastic blood impermeable membrane;
    at least one scaffolding element extended from a vertex of said conical elastic blood impermeable membrane along a longitudinal axis traversing a center of a conical space encircled by said conical elastic blood impermeable membrane; said at least one scaffolding element comprising a plurality of bended arms connected together at a proximal end and a distal end of the at least one scaffolding element along the longitudinal axis;
    a supporting element for holding said at least one scaffolding element at the center of said conical elastic blood impermeable membrane; and
    a plurality of tilted hooks each having a proximal end attached to said supporting element and a distal end tilted outward from a longitudinal axis crossing via the center of said conical elastic blood impermeable membrane.

12. A method for occluding a blood vessel, comprising:
    conducting a medical implant having an elastic blood impermeable membrane in a compressed state and at least one scaffolding element to an intravascular target area in a blood vessel;
    placing said medical implant in said intravascular target area so that said scaffolding element is extended from said elastic blood impermeable membrane along a longitudinal axis traversing a center of a conical space encircled by said conical elastic blood impermeable membrane; said at least one scaffolding element comprising a plurality of bended arms connected together at a proximal end and a distal end of the at least one scaffolding element along the longitudinal axis; and
    occluding said vessel by spreading said elastic blood impermeable membrane from said compressed state to an uncompressed state in said intravascular target area;
    wherein said at least one scaffolding element is sized and shaped to be attached to at least one blood clot formed at said intravascular target area so that said at least one blood clot being firmly attached to said medical implant.

13. The method of claim 12, wherein said at least one scaffolding element induces encapsulation of said medical implant in said intravascular target area.

14. The method of claim 12, wherein said conducting comprises loading said medical implant into a catheter and using said catheter for performing said conducting.

15. The method of claim 14, wherein said loading comprises:
    placing said medical implant in an adaptor,
    connecting an adaptor to a distal end of a catheter, and
    pulling said medical implant into said catheter, and
    removing said adaptor from the distal end.

16. The method of claim 15, wherein said pulling comprises pulling said medical implant into a magazine in said catheter.

17. The method of claim 15, wherein said medical implant is stored prior to delivery in a non compressed state.

* * * * *